US009221789B2

(12) United States Patent
Chiodo et al.

(10) Patent No.: US 9,221,789 B2
(45) Date of Patent: Dec. 29, 2015

(54) MULTICOMPONENT CRYSTALS COMPRISING IMATINIB MESILATE AND SELECTED CO-CRYSTAL FORMERS

(71) Applicant: BASF SE, Ludwigshafen (DE)

(72) Inventors: Tiziana Chiodo, Mannheim (DE); Rolf Hellmann, Lustadt (DE); Marcus Vossen, Limburgerhof (DE); Beate Salvador, Ellerstadt (DE); Andreas Hafner, Gelterkinden (CH); Tobias Hintermann, Therwil (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/406,264

(22) PCT Filed: Jun. 18, 2013

(86) PCT No.: PCT/EP2013/062579
§ 371 (c)(1),
(2) Date: Dec. 8, 2014

(87) PCT Pub. No.: WO2013/189910
PCT Pub. Date: Dec. 27, 2013

(65) Prior Publication Data
US 2015/0126520 A1 May 7, 2015

Related U.S. Application Data

(60) Provisional application No. 61/662,933, filed on Jun. 22, 2012.

(30) Foreign Application Priority Data

Jun. 22, 2012 (EP) .................... 12173093
Oct. 17, 2012 (EP) .................... 12188814

(51) Int. Cl.
*A61K 31/506* (2006.01)
*C07D 401/04* (2006.01)
*C07C 55/10* (2006.01)
*C07C 57/15* (2006.01)
*C07C 63/06* (2006.01)

(52) U.S. Cl.
CPC .............. *C07D 401/04* (2013.01); *C07C 55/10* (2013.01); *C07C 57/15* (2013.01); *C07C 63/06* (2013.01); *C07B 2200/13* (2013.01)

(58) Field of Classification Search
CPC ............................ C07D 401/14; A61K 31/506
See application file for complete search history.

(56) References Cited

U.S. PATENT DOCUMENTS

| 6,894,051 B1 | 5/2005 | Zimmermann et al. |
| 8,716,305 B2 | 5/2014 | Hafner et al. |
| 8,796,481 B2 | 8/2014 | Berens et al. |
| 8,841,316 B2 | 9/2014 | Hafner et al. |
| 2002/0115858 A1 | 8/2002 | Zimmermann et al. |
| 2005/0192284 A1 | 9/2005 | Zimmermann et al. |
| 2006/0030568 A1 | 2/2006 | Zimmermann et al. |
| 2007/0004746 A1 | 1/2007 | Zimmermann et al. |
| 2008/0132419 A1 | 6/2008 | Rodriguez-Hornedo |
| 2013/0237553 A1 | 9/2013 | Hafner et al. |
| 2013/0251911 A1 | 9/2013 | Schrof et al. |
| 2014/0018461 A1 | 1/2014 | Hintermann et al. |
| 2014/0155371 A1 | 6/2014 | Hafner et al. |
| 2014/0205641 A1 | 7/2014 | Sowa et al. |
| 2015/0018207 A1 | 1/2015 | Knieriem et al. |
| 2015/0099631 A1 | 4/2015 | Reinhard et al. |

FOREIGN PATENT DOCUMENTS

| WO | WO 99/03854 A1 | 1/1999 |
| WO | WO 2004/064762 | 8/2004 |
| WO | WO 2004/078163 A2 | 9/2004 |
| WO | WO 2004/106326 A1 | 12/2004 |
| WO | WO 2005/077933 A1 | 8/2005 |
| WO | WO 2006/054314 A1 | 5/2006 |
| WO | WO 2007/023182 A1 | 3/2007 |
| WO | WO 2007/059963 A1 | 5/2007 |
| WO | WO 2007/136510 A2 | 11/2007 |
| WO | WO 2008/054609 A2 | 5/2008 |
| WO | WO 2010/081443 A2 | 7/2010 |
| WO | WO 2010081443 A2 * | 7/2010 |
| WO | WO 2011/023146 A1 | 3/2011 |
| WO | WO 2012/069394 A1 | 5/2012 |
| WO | WO 2012090221 A1 * | 7/2012 |
| WO | WO 2012/110435 A1 | 8/2012 |
| WO | WO 2012/136606 A1 | 10/2012 |
| WO | WO 2012/143308 A1 | 10/2012 |
| WO | WO 2013/014604 A1 | 1/2013 |

(Continued)

OTHER PUBLICATIONS

M. Veverka et al., 143 Monatshefte für Chemie, 1405-1415 (2012).*
Solid State Characterization of Pharmaceuticals 473-491, 490 (R.A. Storey et al., eds., 2011).*
L. Yu, 48 Advanced Drug Delivery Reviews, 27-42 (2001).*
S. Bates et al., 23 Pharmaceutical Research, 2333-2349 (2006).*
Preformulation in Solid Dosage Form Development at 239-240 (M. C. Adeyeye et al., eds., 2008).*
U.S. Appl. No. 14/428,488, filed Mar. 16, 2015, Hintermann, et al.
U.S. Appl. No. 14/433,147, filed Apr. 2, 2015, Chiodo, et al.
U.S. Appl. No. 13/574,005, filed May 28, 2013, Hafner, et al.
U.S. Appl. No. 14/360,799, filed May 27, 2014, Hafner, et al.
U.S. Appl. No. 14/388,462, filed Sep. 26, 2014, Chiodo, et al.
U.S. Appl. No. 14/406,339, filed Dec. 8, 2014, Chiodo, et al.
U.S. Appl. No. 14/415,875, filed Jan. 20, 2015, Hafner, et al.

(Continued)

Primary Examiner — Alexander R Pagano
(74) Attorney, Agent, or Firm — Oblon, McClelland, Maier & Neustadt, L.L.P.

(57) ABSTRACT

Novel solid forms of imatinib mesilate comprising as active ingredient 4-[(4-methyl-1-piperazinyl)methyl]-N-[4-methyl-3-[[4-(3-pyridinyl)-2-pyrimidinyl]amino]-phenyl]-benzamide methanesulfonic acid salt and as co-crystal former benzoic acid, fumaric acid or succinic acid are described. The said multi-component crystalline forms possess improved physical and biological properties with respect to the crystalline forms of the active pharmaceutical ingredient previously known.

15 Claims, 6 Drawing Sheets

(56) References Cited

FOREIGN PATENT DOCUMENTS

| | | |
|---|---|---|
| WO | WO 2013/030777 A1 | 3/2013 |
| WO | WO 2013/084130 A1 | 6/2013 |
| WO | WO 2013/098370 A1 | 7/2013 |
| WO | WO 2013/124791 A1 | 8/2013 |
| WO | WO 2013/135606 A1 | 9/2013 |
| WO | WO 2013/139851 A1 | 9/2013 |
| WO | WO 2013/143927 A1 | 10/2013 |
| WO | WO 2013/174693 A1 | 11/2013 |
| WO | WO 2013/174694 A1 | 11/2013 |
| WO | WO 2013/186726 A2 | 12/2013 |
| WO | WO 2014/023682 A1 | 2/2014 |
| WO | WO 2014/045148 A1 | 3/2014 |
| WO | WO 2014/060449 A1 | 4/2014 |
| WO | WO 2014/097032 A1 | 6/2014 |
| WO | WO 2014/135392 A1 | 9/2014 |

OTHER PUBLICATIONS

International Search Report issued Jul. 31, 2013 in PCT/EP2013/062579.

European Search Report issued Sep. 18, 2012 in Patent Application No. 12173093.

International Preliminary Report on Patentability and Written Opinion issued Dec. 23, 2014 in PCT/EP2013/062579.

* cited by examiner

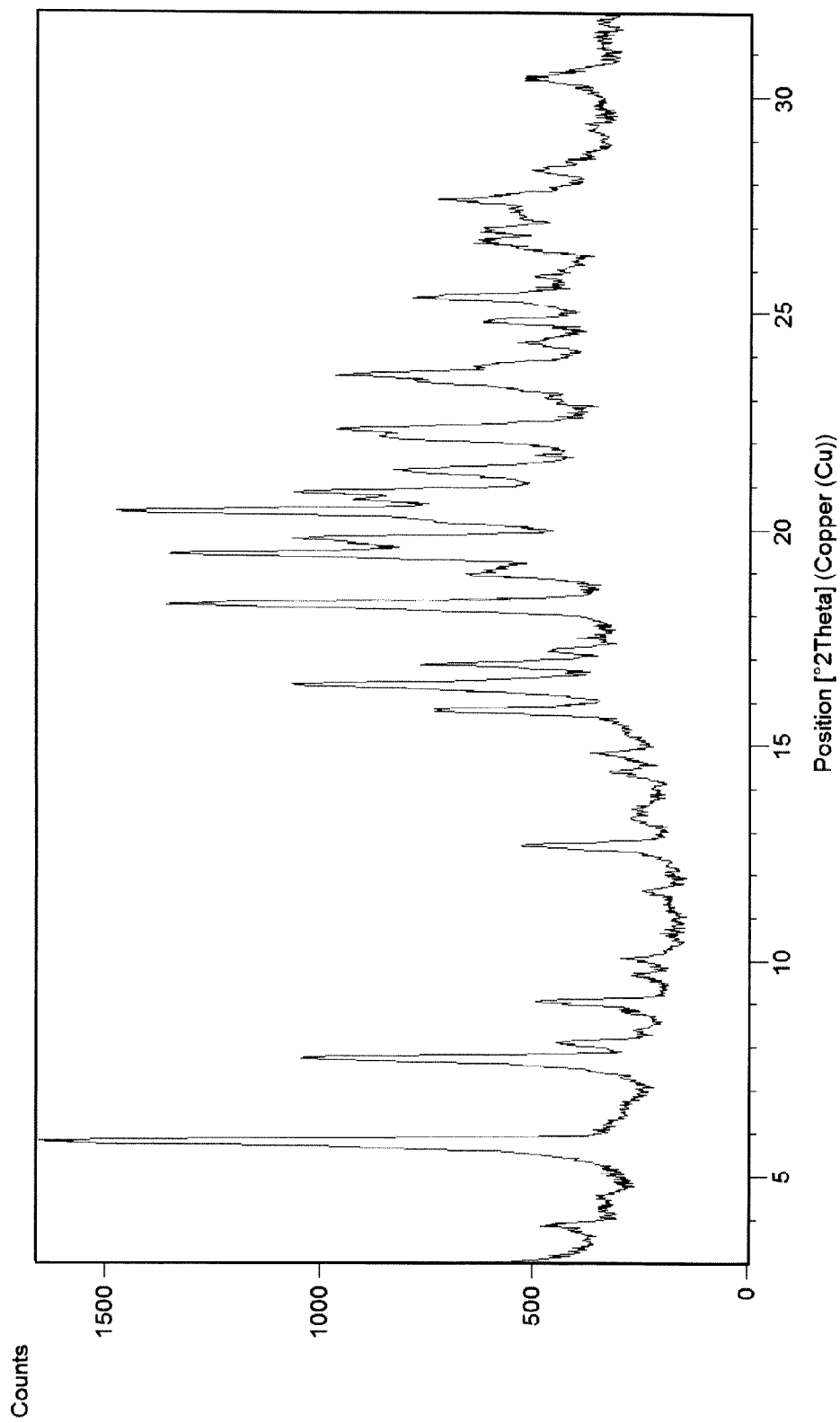
Figure 1. XRPD pattern of the co-crystal comprising imatinib mesilate and benzoic acid

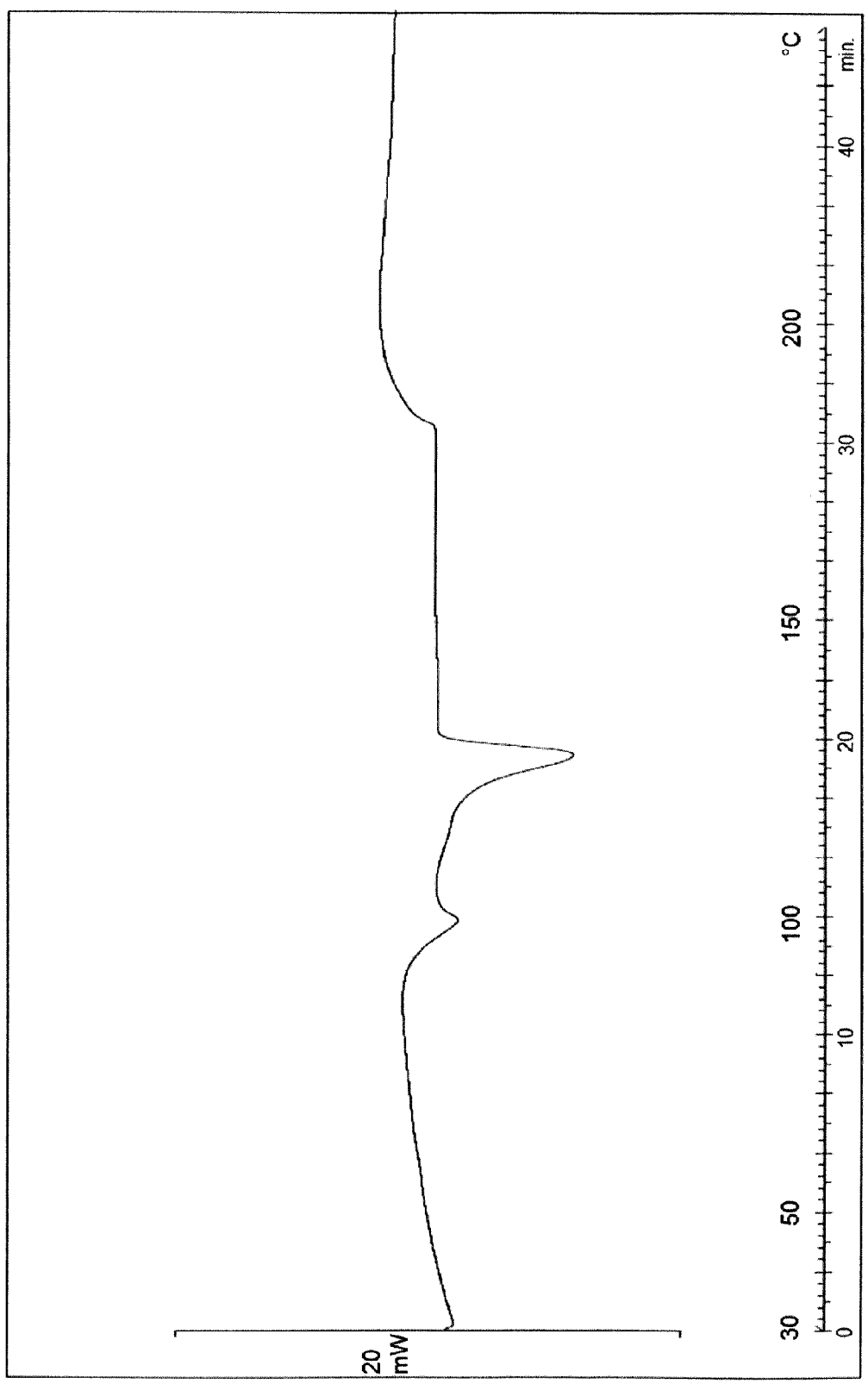
Figure 2. DSC trace of the co-crystal comprising imatinib mesilate and benzoic acid

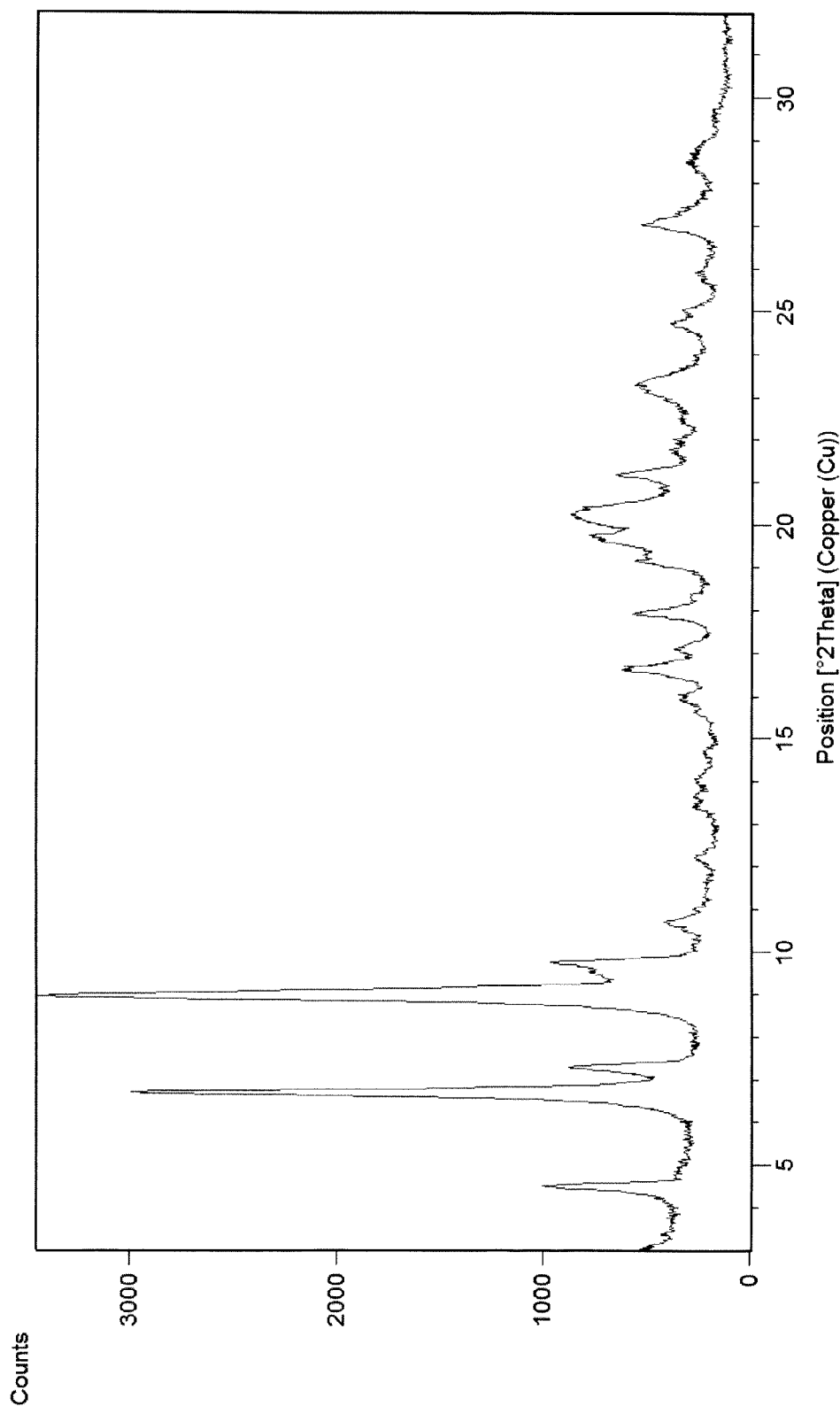
Figure 3. XRPD pattern of the co-crystal comprising imatinib mesilate and fumaric acid

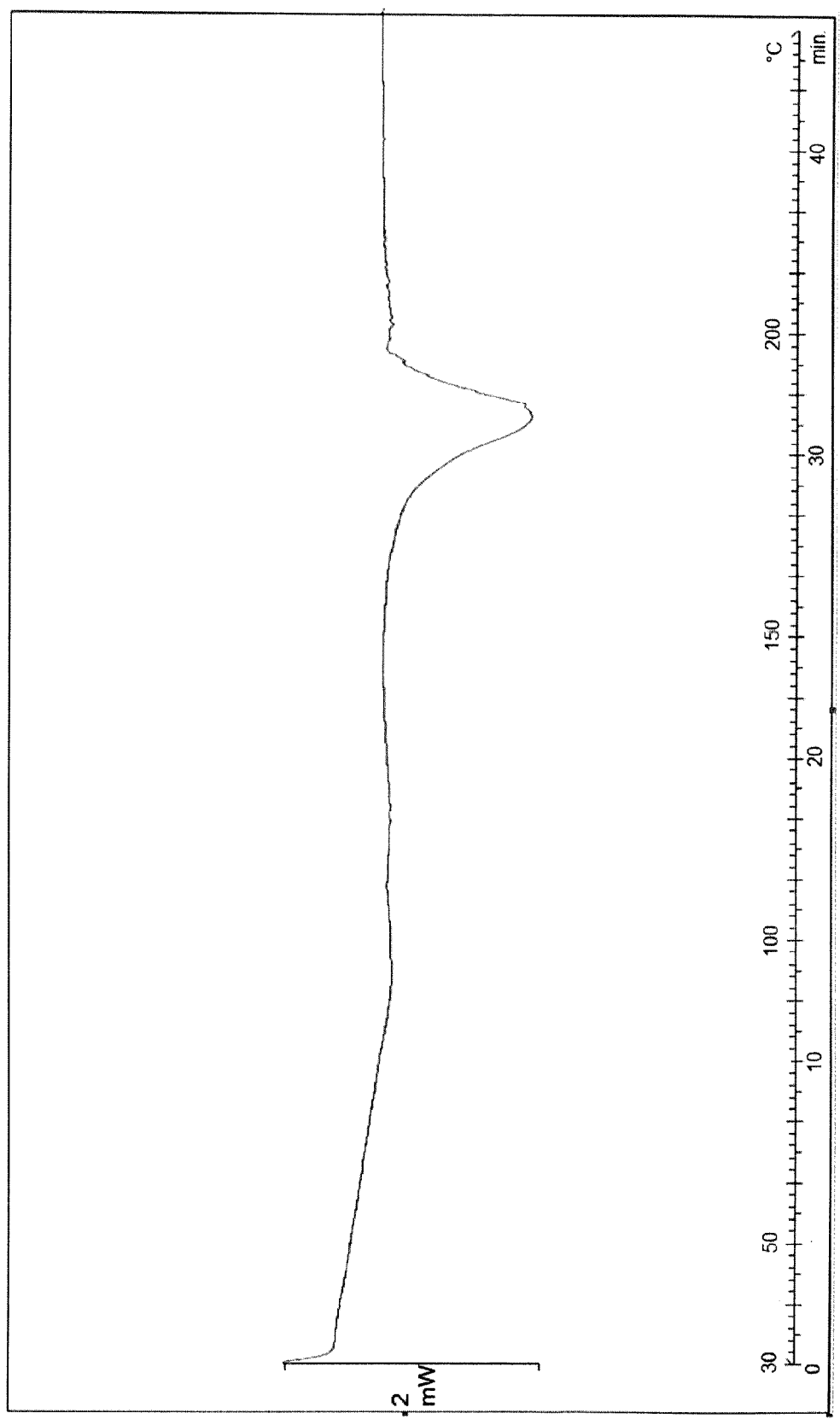
Figure 4. DSC trace of the co-crystal comprising imatinib mesilate and fumaric acid

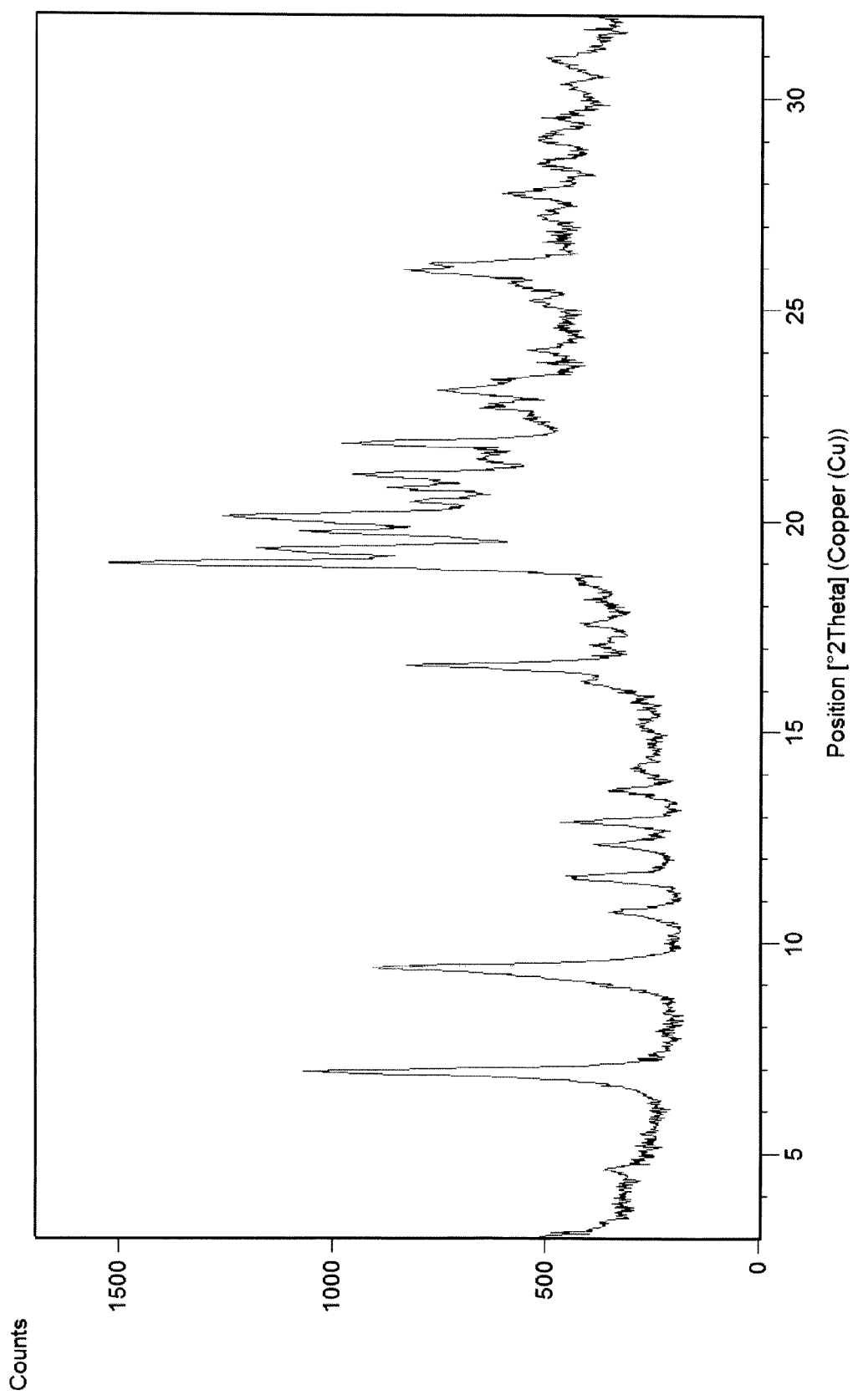
Figure 5. XRPD pattern of the co-crystal comprising imatinib mesilate and succinic acid

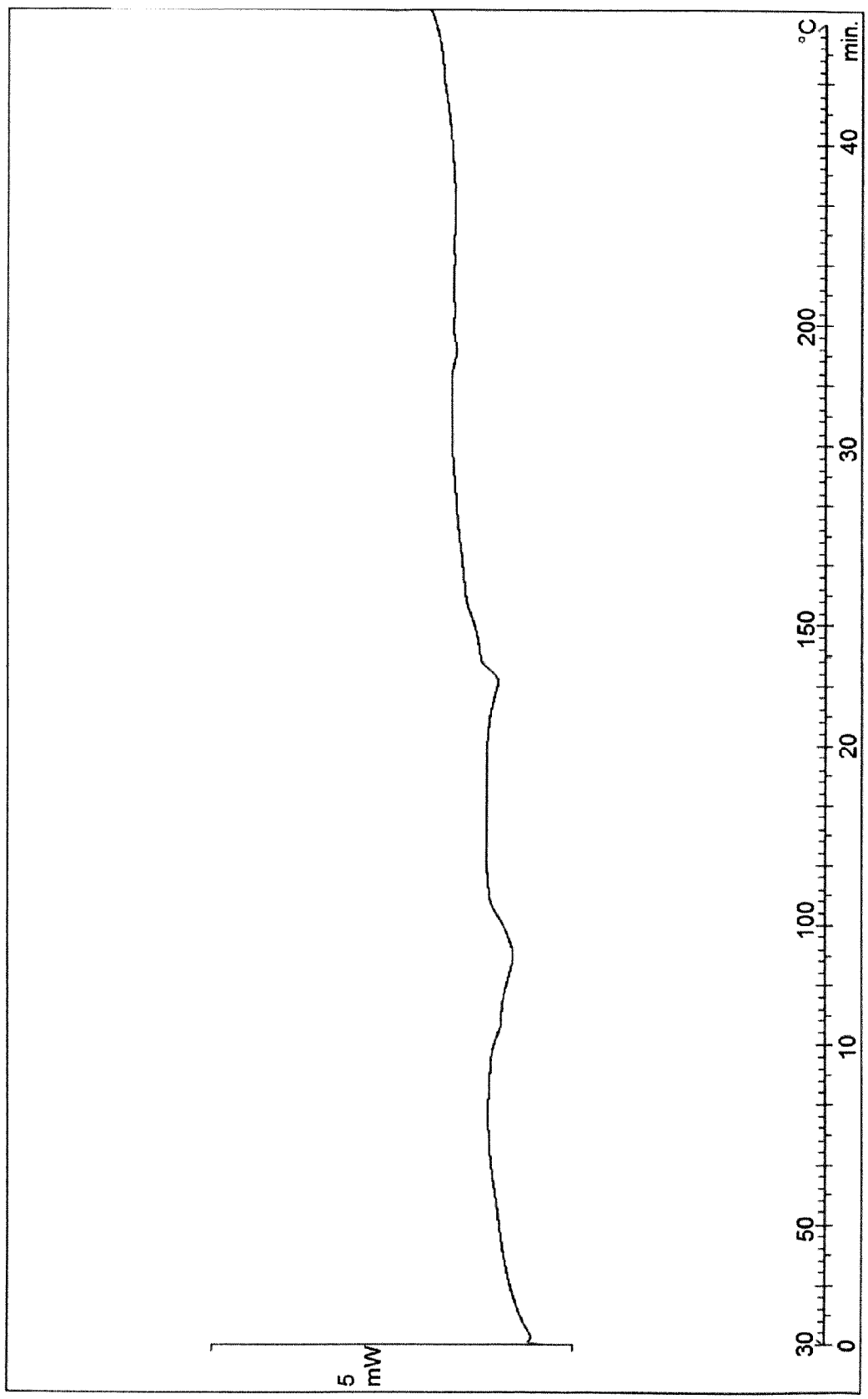
Figure 6. DSC trace of the co-crystal comprising imatinib mesilate and succinic acid

MULTICOMPONENT CRYSTALS COMPRISING IMATINIB MESILATE AND SELECTED CO-CRYSTAL FORMERS

The present invention relates to multicomponent systems comprising imatinib mesilate and selected co-crystal formers, to pharmaceutical preparations comprising said systems, and specifically to homogenous crystalline phases (co-crystals) comprising imatinib mesilate and selected co-crystal formers. The invention also relates to processes for preparing said multicomponent systems and crystalline phases. The invention also relates to compositions comprising said multicomponent systems or crystalline phases and pharmaceutically acceptable carrier and to methods of using said multicomponent systems or crystalline phases to treat a disease condition wherein tyrosine kinase inhibition is beneficial.

The active substance imatinib mesilate is the mesylate salt form of imatinib, the synosymus of 4-[(4-methyl-1-piperazinyl)methyl]-N-[4-methyl-3-[[4-(3-pyridinyl)-2-pyrimidinyl]amino]-phenyl]-benzamide methanesulfonic acid salt, specifically shown in formula (1):

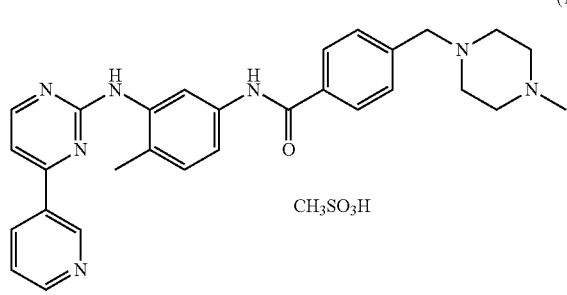

(1)

Imatinib mesilate is known to act as as a tyrosine kinase inhibitor that selectively inhibits the Abl tyrosine kinases. It is useful for the treatment of chronic myelogenous leukemia (CML) and gastrointestinal stromal tumors (GISTs) and is marketed as Glivec® (Europe, Australia, Latin America) or Gleevec® (USA). Imatinib mesilate may have different polymorphic phases.

In WO 99/03854 are disclosed crystalline forms, hereafter referred as from α and form β of 4-[(4-methyl-1-piperazinyl)methyl]-N-[4-methyl-3-[[4-(3-pyridinyl)-2-pyrimidinyl]amino]-phenyl]-benzamide methanesulfonic acid salt.

WO 04/106326 discloses the hydrate crystalline form, hereafter referred as form H1, the corresponding hydrate amorphous phase and a pharmaceutical composition comprising the amorphous imatinib mesilate hydrate.

WO 05/077933, WO 06/054314, WO 07/059963, WO 07/023182 and WO 07/136510 disclose further crystalline forms of imatinib mesilate, the processes to prepare them and the corresponding pharmaceutical compositions.

WO 10/081443 discloses dosage forms of tyrosine kinase inhibitors. Co-crystals comprising imatinib mesilate and arginine, lactose, guanidine, n-methylglucamin, histidine, glucose, lactose, fructose, alginic acid, pectin 4 are mentioned.

WO 11/023146 discloses a process to generate imatinib mesilate polymorphs by crystallization in aqueous inorganic solution. Cocrystals with the inorganic salts NaCl, KCl, KBr are described.

Though there are a number of solid forms of imatinib mesilate known, there exists a need for other solid forms, especially crystalline forms, of 4-[(4-methyl-1-piperazinyl)methyl]-N-[4-methyl-3-[[4-(3-pyridinyl)-2-pyrimidinyl]amino]-phenyl]-benzamide methanesulfonic acid salt for sufficient diversity on crystalline materials to optimize manufacture, improve hygroscopic behavior, dissolution rate, formulation and biological efficiency.

SUMMARY OF THE INVENTION

The invention provides the description of novel crystalline forms of imatinib mesilate comprising imatinib mesilate and selected co-crystal formers, and processes for manufacture thereof.

The said crystalline forms show improved physical and/or biological characteristics which may assist in the manufacture or formulation of the active compound and to achieve the purity levels and uniformity required for regulatory approval. The said crystalline form may possess improved pharmacological characteristics, for example, improved bioavailability and/or hygroscopic behaviour, thus offering enhanced possibilities to modulate and design improved drug products.

DETAILED DESCRIPTION OF THE INVENTION

The solid form of the invention is a composite comprising two components, which are the adduct salt of imatinib with methanesulfonic acid (i.e. imatinib mesilate) and a carbonic acid compound (i.e. carboxylic acid) selected from benzoic acid, fumaric acid and succinic acid, within one single phase. Imatinib mesilate and one of benzoic acid, fumaric acid, succinic acid are present in the same solid phase, preferably in the same crystalline phase, i.e. forming a co-crystal (the pKa values of the present carboxylic acid component are from a range defining the product as a co-crystal rather than a salt).

The molar ratio of imatinib mesilate and benzoic acid, fumaric acid or succinic acid is generally in the range from about 2:1 to about 1:2. The term "about" in this context refers to small deviations in the molar ratio, which may lead to deviations from the given ratio typically in the range of 10%. In particular, the molar ratio typically is about 1:2 (e.g. ranging from 1:1.8 to to 1:2.2) for the imatinib mesilate and benzoic acid cocrystal, and from 1.5:1 to 1:1.5 and especially about 1:1 (i.e. from 1.1:1 to 1:1.1) for the imatinib mesilate and fumaric acid, or imatinib mesilate and succinic acid cocrystal. Similarly, the composition of the present invention may show a deviation from the original 1:1 molar ratio, which may result in that the component imatinib mesitylate in the present product shows a final molar ratio of imatinib:methylsulfonic acid from the range 1.1:1 to 0.9:1, especially 1.1:1 to 1:1.

The invention thus includes
a) a multicomponent molecular crystal containing 4-[(4-methyl-1-piperazinyl)methyl]-N-[4-methyl-3-[[4-(3-pyridinyl)-2-pyrimidinyl]amino]-phenyl]-benzamide methanesulfonic acid salt and benzoic acid, especially
b) an anydrous crystalline form as defined under (a) consisting essentially of 4-[(4-methyl-1-piperazinyl) methyl]-N-[4-methyl-3-[[4-(3-pyridinyl)-2-pyrimidinyl]amino]-phenyl]-benzamide methanesulfonic acid salt and benzoic acid, having stoichiometric ratio 1:2;
c) a multicomponent molecular crystal containing 4-[(4-methyl-1-piperazinyl)methyl]-N-[4-methyl-3-[[4-(3-pyridinyl)-2-pyrimidinyl]amino]-phenyl]-benzamide methanesulfonic acid salt and fumaric acid, especially
d) an anydrous crystalline form as defined under (c) consisting essentially of 4-[(4-methyl-1-piperazinyl) methyl]-N-[4-methyl-3-[[4-(3-pyridinyl)-2-pyrimidinyl]amino]-phenyl]-benzamide methanesulfonic acid salt and fumaric acid, having stoichiometric ratio 1:1;

e) a multicomponent molecular crystal containing 4-[(4-methyl-1-piperazinyl) methyl]-N-[4-methyl-3-[[4-(3-pyridinyl)-2-pyrimidinyl]amino]-phenyl]-benzamide methanesulfonic acid salt and succinic acid, especially f) an anydrous crystalline form as defined under (e) consisting essentially of 4-[(4-methyl-1-piperazinyl) methyl]-N-[4-methyl-3-[[4-(3-pyridinyl)-2-pyrimidinyl]amino]-phenyl]-benzamide methanesulfonic acid salt and succinic acid, having stoichiometric ratio 1:1.

The co-crystal with benzoic acid, especially the solid form defined under (a), may be further characterized by its melting range 117-137° C., preferably 124-130° C., or its m.p. of 127° C. The present solid form provides better dissolution characteristic and hygroscopic behavior, when compared with the imatinib mesilate forms previously known.

Imatinib mesilate and benzoic acid are present in the same solid phase, preferably in the same crystalline phase, i.e. forming a co-crystal. The preferred novel crystalline form generally exhibits a characteristic X-ray powder diffraction pattern with characteristic peaks expressed in d-values (Å): 15.09 (vs), 11.37 (vs), 10.88 (m), 9.74 (m), 6.96 (m), 5.61 (m), 5.41 (s), 5.26 (m), 4.87 (vs), 4.57 (vs), 4.48 (m), 4.35 (vs), 4.25 (s), 4.16 (m), 4.02 (m), 3.98 (m), 3.78 (m), 3.51 (m).

Solid form defined under (a) comprises comprises a crystalline form of 4-[(4-methyl-1-piperazinyl)methyl]-N-[4-methyl-3-[[4-(3-pyridinyl)-2-pyrimidinyl]amino]-phenyl]-benzamide methanesulfonic acid salt and benzoic acid, having stoichiometric ratio of about 1:2, which exhibits a characteristic X-ray powder diffraction pattern with characteristic peaks expressed in d-values (Å) as shown in the below table:

| d value [Angstroem] | Intensity |
|---|---|
| 22.63 | w |
| 15.09 | vs |
| 11.37 | vs |
| 10.88 | m |
| 9.74 | m |
| 6.96 | m |
| 6.14 | w |
| 5.99 | w |
| 5.61 | m |
| 5.41 | s |
| 5.26 | m |
| 4.87 | vs |
| 4.69 | w |
| 4.57 | vs |
| 4.48 | m |
| 4.35 | vs |
| 4.25 | s |
| 4.16 | m |
| 4.02 | m |
| 3.98 | m |
| 3.78 | m |
| 3.66 | w |
| 3.59 | w |
| 3.51 | m |

Here and in the following the abbreviations in brackets mean: (vs)=very strong intensity; (s)=strong intensity; (m)=medium intensity; (w)=weak intensity.

Also preferred is the crystalline form of 4-[(4-methyl-1-piperazinyl) methyl]-N-[4-methyl-3-[[4-(3-pyridinyl)-2-pyrimidinyl]amino]-phenyl]-benzamide methanesulfonic acid salt and benzoic acid, having stoichiometric ratio of about 1:2, which exhibits a characteristic X-ray powder diffraction pattern substantially as shown in FIG. 1.

The co-crystal with fumaric acid, especially the solid form defined under (c), may be further characterized by its melting point of 186° C. (e.g. from melting range 176-196° C., especially 183-189° C.). The present solid form provides better hygroscopic behavior, when compared with the imatinib mesilate forms previously known.

Imatinib mesilate and fumaric acid are present in the same solid phase, preferably in the same crystalline phase, i.e. forming a co-crystal. The preferred novel crystalline form generally exhibits a characteristic X-ray powder diffraction pattern with characteristic peaks expressed in d-values (Å): 19.54 (m), 13.11 (vs), 12.08 (m), 9.85 (s), 9.05 (m).

Solid form defined under (c) comprises comprises a crystalline form of 4-[(4-methyl-1-piperazinyl)methyl]-N-[4-methyl-3-[[4-(3-pyridinyl)-2-pyrimidinyl]amino]-phenyl]-benzamide methanesulfonic acid salt and fumaric acid, having stoichiometric ratio 1:1, which exhibits a characteristic X-ray powder diffraction pattern with characteristic peaks expressed in d-values (Å) as shown in the below table:

| d value [Angstroem] | Intensity |
|---|---|
| 19.54 | m |
| 13.11 | vs |
| 12.08 | m |
| 9.85 | S |
| 9.05 | m |
| 8.27 | w |
| 5.32 | w |
| 4.95 | w |
| 4.50 | w |
| 4.36 | w |
| 4.20 | w |
| 3.81 | w |
| 3.31 | w |

Here and in the following the abbreviations in brackets mean: (vs)=very strong intensity; (s)=strong intensity; (m)=medium intensity; (w)=weak intensity.

Also preferred is the crystalline form of 4-[(4-methyl-1-piperazinyl) methyl]-N-[4-methyl-3-[[4-(3-pyridinyl)-2-pyrimidinyl]amino]-phenyl]-benzamide methanesulfonic acid salt and fumaric acid, having stoichiometric ratio 1:1, which exhibits a characteristic X-ray powder diffraction pattern substantially as shown in FIG. 3.

The co-crystal with succinic acid, especially the solid form defined under (e) may be further characterized by its melting range of 140° C.-160° C. The relatively broad melting range and a further endothermical transition in the range 90-100° C. indicate the existence of polymorphic phases of the defined multicomponent system. The present solid form provides better dissolution characteristic and hygroscopic behavior, when compared with the imatinib mesilate forms previously known.

Imatinib mesilate and succinic acid are present in the same solid phase, preferably in the same crystalline phase, i.e. forming a co-crystal. The preferred novel crystalline form generally exhibits a characteristic X-ray powder diffraction pattern with characteristic peaks expressed in d-values (Å): 12.68 (vs), 9.38 (s), 5.34 (m), 4.68 (vs), 4.58 (s), 4.50 (s), 4.41 (s), 4.21 (m), 4.07 (m).

Solid form defined under (e) comprises a crystalline form of 4-[(4-methyl-1-piperazinyl)methyl]-N-[4-methyl-3-[[4-(3-pyridinyl)-2-pyrimidinyl]amino]-phenyl]-benzamide methanesulfonic acid salt and succinic acid, having stoichiometric ratio 1:1, which exhibits a characteristic X-ray powder diffraction pattern with characteristic peaks expressed in d-values (Å) as shown in the below table:

| d value [Angstroem] | Intensity |
|---|---|
| 18.96 | w |
| 12.68 | vs |
| 9.38 | s |
| 8.23 | w |
| 7.64 | w |
| 7.17 | w |
| 6.86 | w |
| 6.49 | w |
| 6.28 | w |
| 5.34 | m |
| 4.68 | vs |
| 4.58 | s |
| 4.50 | s |
| 4.41 | s |
| 4.21 | m |
| 4.07 | m |
| 3.85 | w |
| 3.44 | w |
| 3.22 | w |

Here and in the following the abbreviations in brackets mean: (vs)=very strong intensity; (s)=strong intensity; (m)=medium intensity; (w)=weak intensity.

Also preferred is the crystalline form of 4-[(4-methyl-1-piperazinyl) methyl]-N-[4-methyl-3-[[4-(3-pyridinyl)-2-pyrimidinyl]amino]-phenyl]-benzamide methanesulfonic acid salt and succinic acid, having stoichiometric ratio 1:1, which exhibits a characteristic X-ray powder diffraction pattern substantially as shown in FIG. 5.

Another object of the invention is a process for the preparation of crystalline form defined under (a) to (f) which comprises the steps of i) providing a solution of imatinib mesilate (e.g. imatinib mesilate form β) and benzoic acid, fumaric acid or succinic acid in a suitable solvent, ii) cooling or concentrating the solution provided in steps (i), and iii) separating the precipitate and drying.

Suitable solvents that may be used in step (i) are typically organic solvents having a water miscibility of at least 10% at room temperature ("polar organic solvents") or mixtures of water with polar organic solvents. Solutions according to steps (i) preferably are concentrated solutions. The concentration of imatinib mesilate may range from 0.1 to about 300 mg/ml of solvents (including water), preferably from 20 to 200 mg/ml.

The process is preferably carried out in the temperature range 25-100° C., preferably 25-80° C., for example at ambient temperature. In a preferred process, step (i) and (ii) are carried out at a temperature from the range 25-80° C. or the mixture is heated to a temperature from said range, e.g. about 80° C., especially in case that solid imatinib mesilate provided in step (i), with forming a solution. The solution thus tempered is then preferably cooled before step (iii).

Ambient temperature means in the context of the invention a temperature range at room temperature or slightly above, comprising 20 to 30° C. and preferably about 23 to 26° C.

Cocrystal defined under a), c) and e) are isolated by filtering off the crystals and drying or by evaporation of the solvent, e.g. in vacuum, an inert gas flow or both at ambient temperature, or elevated temperatures up to 80° C.

Cocrystal defined under a), c) and e) enable to improve the hygroscopic behaviour of imatinib mesilate, i.e. providing a better long-term stability over a broad range of humidity range with respect to the previously known imatinib mesilate forms.

Cocrystal defined under a) and e) enables to improve the dissolution characteristics of imatinib mesilate, i.e. providing a better dissolution kinetic profile with respect to the previously known imatinib mesilate form.

Cocrystal defined under a), c) and e) are thermodynamically stable and can be dried at elevated temperatures, e.g. below 80° C., and is obtained as a fine powder with typical particle size distributions with the median size between 1 and 50 μm, preferably between 1 to 10 μm. This particle size range ensures a fast dissolution profile, while retaining the favourable handling properties in the formulation process.

Cocrystal defined under a) to e) may be used in pharmaceutical compositions in the same way as other forms of imatinib mesilate previously known.

The present invention is also directed to a pharmaceutical composition comprising a solid form containing benzoic acid, fumaric acid or succinic acid and 4-[(4-methyl-1-piperazinyl)methyl]-N-[4-methyl-3-[[4-(3-pyridinyl)-2-pyrimidinyl]amino]-phenyl]-benzamide methanesulfonic acid salt and a pharmaceutically acceptable carrier or diluent.

The amount of solid (especially crystalline) forms of 4-[(4-methyl-1-piperazinyl)methyl]-N-[4-methyl-3-[[4-(3-pyridinyl)-2-pyrimidinyl]amino]-phenyl]-benzamide methanesulfonic acid salt thereof substantially depends on type of formulation and desired dosages during administration time periods. The amount in an oral formulation may be from 0.1 to 200 mg, preferably from 0.5 to 100 mg, and more preferably from 1 to 50 mg.

The present invention thus further provides a therapeutic method for producing an disease condition wherein tyrosine kinase inhibition is beneficial, which method comprises administering in need of such therapy, an effective amount of the crystalline material, especially co-crystal, of the invention as described above.

Oral formulations may be solid formulations such as capsules, tablets, pills and troches, or liquid formulations such as aqueous suspensions, elixirs and syrups. Solid and liquid formulations encompass also incorporation of the present solid form into liquid or solid food.

The solid forms according to the invention may be directly used as powders (micronized particles), granules, suspensions or solutions, or they may be combined together with other pharmaceutically acceptable ingredients in admixing the components and optionally finely divide them, and then filling capsules, composed for example from hard or soft gelatine, compressing tablets, pills or troches, or suspend or dissolve them in carriers for suspensions, elixirs and syrups. Coatings may be applied after compression to form pills.

Pharmaceutically acceptable ingredients are well known for the various types of formulation and may be for example binders such as natural or synthetic polymers, excipients, lubricants, surfactants, sweetening and flavouring agents, coating materials, preservatives, dyes, thickeners, adjuvants, antimicrobial agents and carriers for the various formulation types.

Examples for binders are gum tragacanth, acacia, starch, gelatine, and biological degradable polymers such as homo- or co-polyesters of dicarboxylic acids, alkylene glycols, polyalkylene glycols and/or aliphatic hydroxyl carboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol und esters or -ethers thereof, poly-vinylimidazole, poly-vinylpyrrolidon, und natural polymers like chitosan, carragenan or hyaluronic aid.

Examples for excipients are phosphates such as dicalcium phosphate.

Examples for lubricants are natural or synthetic oils, fats, waxes, or fatty acid salts like magnesium stearate.

Surfactants may be anionic, anionic, amphoteric or neutral. Examples for surfactants are lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Examples for sweetening agents are sucrose, fructose, lactose or aspartam.

Examples for flavouring agents are peppermint, oil of wintergreen or fruit flavours like cherry or orange flavour.

Examples for coating materials gelatine, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for liquid carriers are water, alcohols such as ethanol, glycerol, propylene glycol, liquid polyethylene glycols, triacetin and oils. Examples for solid carriers are talc, clay, microcrystalline cellulose, silica, alumina and the like.

The formulation according to the invention may also contain isotonic agents, such as sugars, buffers or sodium chloride.

Colloidal silicon dioxide may be contained for use as a glidant, carrier, desiccant. Crospovidone may be contained for use as a disintegrant. Hydroxypropyl methylcellulose may be contained for use as a binder. Magnesium stearate may be contained for use as a lubricant. Microcrystalline cellulose may be contained for use as a carrier.

Pharmaceutical compositions of the present invention can optionally be mixed with other forms of imatinib mesylate and/or other active ingredients. In addition, pharmaceutical compositions of the present invention can contain inactive ingredients such as diluents, carriers, fillers, bulking agents, binders, disintegrants, disintegration inhibitors, absorption accelerators, wetting agents, lubricants, glidants, surface active agents, flavoring agents, and the like. Diluents increase the bulk of a solid pharmaceutical composition and can make a pharmaceutical dosage form containing the composition easier for the patient and care giver to handle. Diluents for solid compositions include, for example, microcrystalline cellulose (e.g., Avicel®), micro:fine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®_}, potassium chloride, powdered cellulose, sodium chloride, sorbitol, or talc. Carriers for use in the pharmaceutical compositions may include, but are not limited to, lactose, white sugar, sodium chloride, glucose, urea, starch, calcium carbonate, kaolin, crystalline cellulose, or silicic acid.

Binders help bind the active ingredient and other excipients together after compression. Binders for solid pharmaceutical compositions include for example acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel~, hydroxypropyl methyl cellulose (e.g. Methocel®_>, liquid glucose, magnesium aluminum silicate, maltodextrin, methylcellulose, polymethacrylates, povidone (e.g. Kollidon®, Plasdone~, pregelatinized starch, sodium alginate, or starch. 41 Disintegrants can increase dissolution. Disintegrants include, for example, alginic acid, carboxymethylcellulose calcium, carboxymethylcellulose sodium (e.g. Ac-Di-Sol®, Primellose~, colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab~ and starch. Disintegration inhibitors may include, but are not limited to, white sugar, stearin, coconut butter, hydrogenated oils, and the like. Absorption accelerators may include, but are not limited to, quaternary ammonium base, sodium laurylsulfate, and the like. Wetting agents may include, but are not limited to, glycerin, starch, and the like. Adsorbing agents may include, but are not limited to, starch, lactose, kaolin, bentonite, colloidal silicic acid, and the IiJ~e. A lubricant can be added to the composition to reduce adhesion and ease release of the product from a punch or dye during tableting. Lubricants include for example magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate. Glidants can be added to improve the flowability of non-compacted solid composition and improve the accuracy of dosing. Excipients that can function as glidants include for example colloidal silicon dioxide, magnesium trisilicate, powdered cellulose, starch, talc and tribasic calcium phosphate. Flavoring agents and flavor enhancers make the dosage form more palatable to the patient. Common flavoring agents and flavor enhancers for pharmaceutical products that can be included in the composition of the present invention include for example maltol, vanillin, ethyl vanillin, menthol, citric acid, fumaric acid, ethyl maltol, and tartaric acid. Tablets can be further coated with commonly known coating materials such as sugar coated tablets, gelatin film coated tablets, tablets coated with enteric coatings, tablets coated with films, double layered tablets, and multi-layered tablets.

Capsules can be coated with shell made, for example, from gelatin and optionally contain a plasticizer such as glycerin and sorbitol, and an opacifying agent or colorant. Solid and liquid compositions can also be dyed using any pharmaceutically acceptable colorant to improve their appearance and/or facilitate patient identification of the product and unit dosage level. In liquid pharmaceutical compositions of the present invention, the imatinib mesylate of the present invention is suspended together with any other solid ingredients, which may be dissolved or suspended, in a liquid carrier, such as water, vegetable oil, alcohol, polyethylene glycol, propylene glycol or glycerin. In suspension the Imatinib mesylate retains its crystalline form. Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol. Liquid pharmaceutical compositions of the present invention can also contain viscosity enhancing agents to improve the mouth-feel of the product and/or coat the lining of the gastrointestinal tract. Such agents include for example acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste. Preservatives and chelating agents such as alcohol, sodium benzoate, butylated hydroxy toluene, butylated hydroxyanisole and ethylenediamine tetraacetic acid can be added at safe levels to improve storage stability.

A liquid pharmaceutical composition according to the present invention can also contain a buffer such as guconic acid, lactic acid, citric acid or acetic acid, sodium guconate, sodium lactate, sodium citrate or sodium acetate.

Selection of excipients and the amounts to use can be readily determined by an experienced formulation scientist in view of standard procedures and reference works known in the art. A composition for tableting or capsule filing can be prepared by wet granulation. In wet granulation some or all of the active ingredients and excipients in powder form are blended and then further mixed in the presence of a liquid, typically water, which causes the powders to clump up into granules. The granulate is screened and/or milled, dried and then screened and/or milled to the desired particle size. The granulate can then be tableted or other excipients can be added prior to tableting, such as a glidant and/or a lubricant. A tableting composition can be prepared conventionally by dry blending. For instance, the blended composition of the actives and excipients can be compacted into a slug or a sheet and then comminuted into compacted granules. The compacted granules can be compressed subsequently into a tablet. As an alternative to dry granulation, a blended composition can be compressed directly into a compacted dosage form using direct compression techniques. Direct compression produces a more uniform tablet without granules. Excipients that are particularly well-suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting. A capsule filling of the present invention can comprise any of the aforementioned blends and granulates that were described with reference to tableting, only they are not subjected to a final tableting step. When shaping the pharmaceutical composition into pill form, any commonly known excipient used in the art can be used. For example, carriers include, but are not limited to, lactose, starch, coconut butter, hardened vegetable oils, kaolin, talc, and the like. Binders used include, but are not limited to, gum arabic powder, tragacanth gum powder, gelatin, ethanol, and the like. Disintegrating agents used include, but are not limited to, agar, laminalia, and the like. For the purpose of shaping the pharmaceutical composition in the form of suppositories, any commonly known excipient used in the art can be used. For example, excipients include, but are not limited to, polyethylene glycols, coconut butter, higher alcohols, esters of higher alcohols, gelatin, semisynthesized glycerides, and the like. When preparing injectable pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic. Additional ingredients, such as dissolving agents, buffer agents, and analgesic agents may be added. If necessary, coloring agents, preservatives, perfumes, seasoning agents, sweetening agents, and other medicines may also be added to the desired preparations during the treatment. The amount of imatinib mesylate of the present invention contained in a pharmaceutical composition according to the present invention is not specifically restricted; however, the dose should be sufficient to treat, ameliorate, or reduce the condition.

The solid forms according to the invention may also be formulated as effervescent tablet or powder, which disintegrate in an aqueous environment to provide a drinking solution.

A syrup or elixir may contain the polymorph of the invention, sucrose or fructose as sweetening agent a preservative like methylparaben, a dye and a flavouring agent.

The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the art of pharmacy.

Dosage forms include solid dosage forms, like tablets, powders, capsules, suppositories, sachets, troches and losenges as well as liquid suspensions and elixirs. While the description is not intended to be limiting, the invention is also not intended to pertain to true solutions of imatinib mesilate whereupon the properties that distinguish the solid forms of imatinib mesilate are lost. However, the use of the novel forms to prepare such solutions is considered to be within the contemplation of the invention.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

Slow release formulations may also be prepared from the crystal form according to the invention in order to achieve a controlled release of the active agent in contact with the body fluids in the gastro intestinal tract, and to provide a substantial constant and effective level of the active agent in the blood plasma. The crystal forms may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

The crystal forms of the invention are also useful for administering a combination of therapeutic effective agents to an animal. Such a combination therapy can be carried out in using at least one further therapeutic agent which can be additionally dispersed or dissolved in a formulation.

The crystal forms of this invention and its formulations respectively can be also administered in combination with other therapeutic agents that are effective to treat a given condition to provide a combination therapy.

The crystal forms and the pharmaceutical composition according to the invention are highly suitable for effective treatment of disorders in connection with need of inhibiting the AbI tyrosine kinases. Imatinib mesilate as well as the present forms, especially co-crystals, thereof and pharmaceutical composition are useful in the treatment of chronic myelogenous leukemia and gastrointestinal stromal tumors.

An object of the invention is also a therapeutic method for producing an AbI tyrosine kinase inhibiting effect in a mammal comprising administering to a mammal in need of such therapy, an effective amount of the present composite containing benzoic acid, fumaric acid or succinic acid and 4-[(4-methyl-1-piperazinyl)methyl]-N-[4-methyl-3-[[4-(3-pyridinyl)-2-pyrimidinyl]amino]-phenyl]-benzamide methanesulfonic acid salt.

The crystalline forms of the invention may be used as single component or as mixtures with other solid forms, which may be crystalline or amorphous.

As to the previously known polymorphic forms of imatinib mesilate it is preferred that these contain 25-100% by weight, especially 50-100% by weight, of at least one of the novel forms, based on the total amount of imatinib mesilate. Preferably, such an amount of the novel polymorphic forms of imatinib mesilate is 75-100% by weight, especially 90-100% by weight. Highly preferred is an amount of 95-100% by weight.

Another object of the invention is a method of delivering a solid form of 4-[(4-methyl-1-piperazinyl)methyl]-N-[4-methyl-3-[[4-(3-pyridinyl)-2-pyrimidinyl]amino]-phenyl]-benzamide methanesulfonic acid salt to a host, which method comprises administering to a host an effective amount of said solid forms, according to the invention.

A further object of the invention is the use the said crystalline forms containing benzoic acid, fumaric acid or succinic acid and 4-[(4-methyl-1-piperazinyl)methyl]-N-[4-methyl-3-[[4-(3-pyridinyl)-2-pyrimidinyl]amino]-phenyl]-benzamide methanesulfonic acid salt, for the manufacture of a medicament useful in the treatment of disorders in connection with need of inhibiting the AbI tyrosine kinases and especially useful in the treatment of chronic myelogenous leukemia and gastrointestinal stromal tumors.

The following examples illustrate the invention.

Wherever noted, room temperature depicts a temperature from the range 18-23° C.; percentages are given by weight, if not indicated otherwise.

Abbreviations:
HPLC high pressure liquid chromatography
NMR nuclear magnetic resonance
FTIR Fourier-transformation infrared spectrometry
PXRD powder x-ray diffraction
XRPD x-ray powder diffractogram
r.h. relative humidity (air, if not indicated otherwise)
m.p. melting point
TG thermogravimetry
v/v volume by volume
Instrumental Powder X-ray diffraction: PXRD is carried out with a Panalytical X'Pert Pro X-ray diffractometer using $Cu_{K-alpha}$ radiation in reflection (Bragg-Brentano) geometry. 2θ values are accurate within an error of ±0.1-0.2°. The samples are prepared without any special treatment other than the application of slight pressure to get a flat surface. The tube voltage is 40 kV and current was 40 mA. The XRPD diffractograms are collected at room temperature in the geometry in the range from 2θ=3°-33° C. with increments of 0.0167° C.

Thermogravimetry:

The thermo gravimetric measurements are carried out with a Mettler Toledo TGA/SDTA851e module. The thermal behaviour is analysed in the range 30-250° C. by using a heating rate of 5° C./min and a stream of nitrogen flowing at 150 ml/during the experiment.

DSC:

DSC is performed on a Mettler Toledo DSC 822e module. The sample is placed in crimped but vented aluminium pans (sample size was 10 mg). The thermal behaviour is analysed in the range 30-250° C. by using a heating rate of 5° C./min and a stream of nitrogen flowing at 150 ml/during the experiment.

1H-NMR:

The 1H-NMR spectra are recorded on a Bruker DPX 300 spectrometer.

Solvent: DMSO-d6.

Experimental

Solvents: For all experiments, Fluka or Merck grade solvents are used.

Co-crystal formers used are

Benzoic Acid obtained from ACROS ORGANICS (#221802500);

Fumaric Acid obtained from ALDRICH (#F1,935-3);

Succinic Acid obtained from MERCK (#8.22260.0250).

For all experiments, imatinib mesilate form β is used, showing a PXRD as of FIG. 2/3 of WO99/03854; m.p. 225° C. Imatinib mesilate form β is prepared as disclosed in WO99/03854, example 1.

EXAMPLE 1

Preparation of the Imatinib Mesilate and Benzoic Acid 334 mg of imatinib mesilate and 166 mg of benzoic acid are suspended in 1 mL of the mixture (v/v) ethanol/water 4:1 at room temperature. The system is stirred for 4 days at room temperature. The resulting suspension is filtered and dried in vacuum for 12 hours. XRPD shows the pattern of FIG. 1. DSC in a closed sample pan shows an endothermal effect with a peak temperature of about 127° C. (65 J/g). 1H-NMR (measured in DMSO-d6) shows the spectrum of a mixture of imatinib mesilate and benzoic acid (molar ratio imatinib mesilate salt:benzoic acid 1:2).

EXAMPLE 2

Preparation of the Imatinib Mesilate and Fumaric Acid 810 mg of imatinib mesilate and 190 mg of fumaric acid are suspended in 20 mL of the mixture (v/v) ethanol/water 96:4 at room temperature. A solution is obtained after refluxing at 80° C. under stirring for 30 minutes, followed by the precipitation of a yellow solid. The mixture is then cooled down to room temperature. The suspension formed is filtered and dried in vacuum for 12 hours. The yield is approximately 68%. XRPD shows the pattern of FIG. 3. DSC in a closed sample pan shows an endothermal effect with a peak temperature of 186° C. (79 J/g). 1H-NMR (measured in DMSO-d6) shows the spectrum of a mixture of imatinib mesilate and fumaric acid (molar ratio imatinib mesilate salt:fumaric acid 1:1).

EXAMPLE 3

Preparation of the Imatinib Mesilate and Succinic Acid 807 mg of imatinib mesilate and 193 mg of succinic acid are suspended in 5 mL of the mixture (v/v) ethanol/water 4:1. The system is stirred for 1 hour at 60° C. A clear solution is obtained. The solution is cooled down to room temperature and no precipitation is observed. The solid is isolated by removing the solvent in vacuum at room temperature. XRPD shows the pattern of FIG. 5. DSC in a closed sample pan shows two endothermal effects with a first peak in the temperature range 90-100° C. and a second peak in the temperature range 140-160° C. 1H-NMR (measured in DMSO-d6) shows the spectrum of a mixture of imatinib mesilate and succinic acid (molar ratio imatinib mesilate salt:succinic acid 1:1).

BRIEF DESCRIPTION OF FIGURES

FIG. 1: Powder X-Ray Diffraction pattern of imatinib mesilate and benzoic acid 1:2 co-crystal FIG. 2: DSC trace of imatinib mesilate and benzoic acid 1:2 co-crystal (range: 30-250° C.)

FIG. 3: Powder X-Ray Diffraction pattern of imatinib mesilate and fumaric acid 1:1 co-crystal FIG. 4: DSC trace of imatinib mesilate and fumaric acid 1:1 co-crystal (range: 30-250° C.)

FIG. 5: Powder X-Ray Diffraction pattern of imatinib mesilate and succinic acid 1:1 co-crystal FIG. 6: DSC trace of imatinib mesilate and succinic acid 1:1 co-crystal (range: 30-250° C.)

The invention claimed is:

1. A crystalline material, comprising 4-[(4-methyl-1-piperazinyl) methyl]-N-[4-methyl-3-[[4-(3-pyridinyl)-2-pyrimidinyl]amino]-phenyl]-benzamide methanesulfonic acid salt and a carboxylic acid compound selected from the group consisting of benzoic acid, fumaric acid, and succinic acid.

2. The crystalline material of claim 1, comprising 4-[(4-methyl-1-piperazinyl)methyl]-N-[4-methyl-3-[[4-(3-pyridinyl)-2-pyrimidinyl]amino]-phenyl]-benzamide methanesulfonic acid salt and the carboxylic acid compound within a same crystalline phase in a molar ratio ranging from 2:1 to 1:2.

3. The crystalline material of claim 1, comprising 4-[(4-methyl-1-piperazinyl)methyl]-N-[4-methyl-3-[[4-(3-pyridinyl)-2-pyrimidinyl]amino]-phenyl]-benzamide methanesulfonic acid salt and benzoic acid within the same crystalline phase, wherein the crystalline material exhibits a X-ray powder diffraction pattern with characteristic peaks expressed in d-values (Å): 15.09, 11.37, 10.88, 9.74, 6.96, 5.61, 5.41, 5.26, 4.87, 4.57, 4.48, 4.35, 4.25, 4.16, 4.02, 3.98, 3.78, 3.51.

4. The crystalline material according to claim 1, which exhibits a X-ray powder diffraction pattern with characteristic peaks expressed in d-values (Å) as shown in the below table:

| d value [Angstrom] | Intensity |
|---|---|
| 22.63 | w |
| 15.09 | vs |
| 11.37 | vs |
| 10.88 | m |
| 9.74 | m |
| 6.96 | m |
| 6.14 | w |
| 5.99 | w |
| 5.61 | m |
| 5.41 | s |
| 5.26 | m |
| 4.87 | vs |
| 4.69 | w |
| 4.57 | vs |
| 4.48 | m |
| 4.35 | vs |
| 4.25 | s |
| 4.16 | m |
| 4.02 | m |
| 3.98 | m |
| 3.78 | m |
| 3.66 | m |
| 3.59 | w |
| 3.51 | m |

5. The crystalline material according to claim 1, comprising 4-[(4-methyl-1-piperazinyl) methyl]-N-[4-methyl-3-[[4-(3-pyridinyl)-2-pyrimidinyl]amino]-phenyl]-benzamide methanesulfonic acid salt and fumaric acid, wherein the crystalline material exhibits a X-ray powder diffraction pattern with characteristic peaks expressed in d-values (Å): 19.54, 13.11, 12.08, 9.85, 9.05.

6. The crystalline material according to claim 1, which exhibits a X-ray powder diffraction pattern with characteristic peaks expressed in d-values (Å) as shown in the below table:

| d value [Angstrom] | Intensity |
|---|---|
| 19.54 | m |
| 13.11 | vs |
| 12.08 | m |
| 9.85 | s |
| 9.05 | m |
| 8.27 | w |
| 5.33 | w |
| 4.95 | w |
| 4.50 | w |
| 4.36 | w |
| 4.20 | w |
| 3.81 | w |
| 3.31 | w |

7. The crystalline material according to claim 1, comprising 4-[(4-methyl-1-piperazinyl)methyl]-N-[4-methyl-3-[[4-(3-pyridinyl)-2-pyrimidinyl]amino]-phenyl]-benzamide methanesulfonic acid salt and succinic acid, wherein the crystalline material exhibits a X-ray powder diffraction pattern with characteristic peaks expressed in d-values (Å): 12.68, 9.38, 5.34, 4.68, 4.58, 4.50, 4.41, 4.21, 4.07.

8. The crystalline material according to claim 1, which exhibits a characteristic X-ray powder diffraction pattern with characteristic peaks expressed in d-values (Å) as shown in the below table:

| d value [Angstrom] | Intensity |
| --- | --- |
| 18.96 | w |
| 12.68 | vs |
| 9.38 | s |
| 8.23 | w |
| 7.64 | w |
| 7.17 | w |
| 6.86 | w |
| 6.49 | w |
| 6.28 | w |
| 5.34 | m |
| 4.68 | vs |
| 4.58 | s |
| 4.50 | s |
| 4.41 | s |
| 4.21 | m |
| 4.07 | m |
| 3.85 | w |
| 3.44 | w |
| 3.22 | w |

9. The crystalline material according to claim 1, comprising a multicomponent molecular crystal comprising 4-[(4-methyl-1-piperazinyl) methyl]-N-[4-methyl-3-[[4-(3-pyridinyl)-2-pyrimidinyl]amino]-phenyl]-benzamide methanesulfonic acid salt and one selected from the group consisting of benzoic acid, fumaric acid and succinic acid, which exhibits a characteristic X-ray powder diffraction pattern as exhibited in FIG. 1 and a characteristic DSC trace as exhibited in FIG. 2; or which exhibits a characteristic X-ray powder diffraction pattern as exhibited in FIG. 3 and a characteristic DSC trace as exhibited in FIG. 4; or which exhibits a characteristic X-ray powder diffraction pattern as exhibited in FIG. 5 and a characteristic DSC trace as exhibited in FIG. 6.

10. A process for the preparation of the crystalline material according to claim 1, comprising
 a) solvating or suspending imatinib mesilate, and benzoic acid, fumaric acid or succinic acid in a suitable solvent,
 b) optionally cooling or concentrating the solution provided in step (a), and
 c) separating a precipitate formed in step (a) or (b) from the solvent and drying.

11. A pharmaceutical composition comprising the crystalline material comprising 4-[(4-methyl-1-piperazinyl)methyl]-N-[4-methyl-3-[[4-(3-pyridinyl)-2-pyrimidinyl] amino]-phenyl]-benzamide methanesulfonic acid salt and the carboxylic acid compound selected from the group consisting of benzoic acid, fumaric acid, and succinic acid within the same crystalline phase according to claim 2, and a pharmaceutically acceptable carrier or diluent.

12. The pharmaceutical composition according to claim 11,
 wherein the carboxylic acid compound is benzoic acid and wherein at least one characteristic peak in an x-ray powder diffractogram expressed in d-values (Å) is selected from the group consisting of 15.09, 11.37, 10.88, 9.74, 6.96, 5.61, 5.41, 5.26, 4.87, 4.57, 4.48, 4.35, 4.25, 4.16, 4.02, 3.98, 3.78, and 3.51; or
 wherein the carboxylic acid compound is fumaric acid and wherein at least one characteristic peak in an x-ray powder diffractogram expressed in d-values (Å) is selected from the group consisting of 19.54, 13.11, 12.08, 9.85, and 9.05; or
 wherein the carboxylic acid compound is fumaric acid and wherein at least one characteristic peak in an x-ray powder diffractogram expressed in d-values (Å) is selected from the group consisting of 12.68, 9.38, 5.34, 4.68, 4.58, 4.50, 4.41, 4.21, and 4.07.

13. A method of delivering 4-[(4-methyl-1-piperazinyl)methyl]-N-[4-methyl-3-[[4-(3-pyridinyl)-2-pyrimidinyl] amino]-phenyl]-benzamide methanesulfonic acid salt, comprising administering an effective amount of the crystalline material according to claim 1 to a host.

14. A medicament, comprising the crystalline material according to claim 1.

15. The medicament according to claim 14, wherein the medicament is useful in the treatment of chronic myelogenous leukemia (CML) and gastrointestinal stromal tumors (GISTs) in connection with a need of inhibiting the Abl tyrosine kinases.

* * * * *